United States Patent [19]

Shum et al.

[11] Patent Number: 5,103,027

[45] Date of Patent: Apr. 7, 1992

[54] OLEFIN EXPOXIDATION USING AN OXORHENIUM PORPHYRIN COMPLEX CATALYST AND AN ORGANIC HYDROPEROXIDE

[75] Inventors: Wilfred P. Shum, West Chester; Haven S. Kesling, Jr., Drexel Hill, both of Pa.

[73] Assignee: Arco Chemical Technology, L.P., Wilmington, Del.

[21] Appl. No.: 734,396

[22] Filed: Jul. 23, 1991

[51] Int. Cl.$^5$ .......................................... C07D 301/19
[52] U.S. Cl. ...................................................... 549/529
[58] Field of Search ........................................ 549/529

[56] References Cited

U.S. PATENT DOCUMENTS

| | | | |
|---|---|---|---|
| 3,316,279 | 4/1967 | Fenton | 260/348.5 |
| 3,351,635 | 11/1967 | Kollar | 260/348.5 |
| 3,360,584 | 12/1967 | Kollar | 549/529 |
| 3,475,499 | 10/1969 | Winnick | 549/529 |
| 3,518,285 | 6/1970 | Fenton et al. | 260/348.5 |
| 3,778,451 | 12/1973 | Poite | 260/348.5 |
| 3,931,249 | 1/1976 | Stautzenberger | 549/529 |
| 4,024,165 | 5/1977 | Shryne et al. | 260/348.5 |
| 4,418,203 | 11/1983 | Kim | 549/531 |
| 4,564,715 | 1/1986 | Briggs et al. | 568/867 |
| 4,822,899 | 4/1989 | Groves et al. | 549/533 |
| 4,987,226 | 1/1991 | Buchler et al. | 540/145 |

FOREIGN PATENT DOCUMENTS

| | | |
|---|---|---|
| 308101 | 3/1989 | European Pat. Off. |
| 308791 | 3/1989 | European Pat. Off. |
| 3902357 | 8/1990 | Fed. Rep. of Germany |
| 7513859 | 4/1976 | Netherlands ............ 549/529 |

OTHER PUBLICATIONS

Bruice, Aldrichimica Acta, vol. 21(4), 87(1988).
Kollar, Preprints, Div. Pet. Chem. 106 (1978).
Ly et al., Chem. Ing. Techn. 61 (8), 646 (1989).
Jorgensen, Chem. Rev. 89 (3), 431 (1989).
Herrmann, J. Organomet. Chem. 382, 1 (1990).
Sheldon, J. Mol. Cat. 7, 107 (1980).
Rummel et al., Oxid. Commun. 6, 319 (1984).
Buchler et al., Chem. Ber. 106, 2710 (1973).
Buchler et al., Z. Naturforsch B. 45, 518 (1990).
Buchler et al., Inorg. Nucl. Letters 8, 1073 (1972).
Murakami, et al., Kenkyu Hokoku–Asahi Garasu Kogyo Gijutsu Shorei Kai 34, 295 (1979) [Chem. Abst. 93, 160405].

Primary Examiner—J. E. Evans
Attorney, Agent, or Firm—Stephen D. Harper

[57] ABSTRACT

Olefins are oxidized to epoxide compounds by contacting the olefins with organic hydroperoxides in the presence of oxorhenium porphyrin complex catalysts. High yields of epoxides are attained, particularly when the olefin substrate bears an aromatic substituent.

20 Claims, No Drawings

OLEFIN EXPOXIDATION USING AN OXORHENIUM PORPHYRIN COMPLEX CATALYST AND AN ORGANIC HYDROPEROXIDE

FIELD OF THE INVENTION

This invention relates to methods wherein an olefin may be oxidized to an epoxide. More particularly, this invention pertains to catalytical epoxidation processes employing rhenium porphyrin complexes as catalysts and organic hydroperoxides as oxidizing agents.

SUMMARY OF THE INVENTION

This invention provides a process for epoxidizing an olefin comprising contacting the olefin with an organic hydroperoxide in the presence of an amount of an oxorhenium (V) porphyrin complex effective to form an epoxide of the olefin. In a preferred embodiment, the process comprises contacting an olefin wherein at least one of the ethylenically unsaturated functional groups of the olefin bears an aromatic substituent with a secondary or tertiary organic hydroperoxide having the general structure

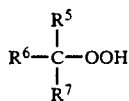

wherein $R^5$, $R^6$, and $R^7$ are the same or different and are selected from the group consisting of hydrogen, methyl, ethyl, and phenyl in the presence of an amount of an oxorhenium (V) porphyrin complex catalyst having the general structure

or

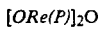

wherein P is a porphyrin ligand and X is an anion selected from the group consisting of halide, alkoxide, phenoxide, hydroxide, perchlorate, thiocyanate, cyanate, and carboxylate effective to form an epoxide of the olefin.

BACKGROUND OF THE INVENTION

Epoxides such as ethylene oxide, propylene oxide, 1,2-butene oxide and the like are useful intermediates for the preparation of a wide variety of products. The oxirane functionality in such compounds is highly reactive and may be ring-opened with any number of nucleophilic reactants. For example, epoxides may be hydrolyzed to yield glycols useful as anti-freeze components, food additives, or reactive monomers for the preparation of condensation polymers such as polyesters.

Polyether polyols generated by the ring-opening polymerization of epoxides are widely utilized as intermediates in the preparation of polyurethane foams, elastomers, sealants, coatings, and the like. The reaction of epoxides with alcohols provides glycol ethers, which may be used as polar solvents in a number of applications.

Many different methods for the preparation of epoxides have been developed. One such method involves the epoxidation of an olefin in a liquid phase reaction using an organic hydroperoxide as the oxidizing agent and certain transition metal compounds as catalyst. Generally speaking, Group IV, V, and VI transition metal compounds have been found to have the highest activity and selectivity in olefin epoxidation reactions using organic hydroperoxides. Metals having low oxidation potentials and high Lewis acidity in their highest oxidation states are superior epoxidation catalysts, according to Sheldon, *J. Mol Cat.* 7, 107(1980). Molybdenum, tungsten, titanium, and vanadium compounds thus have been found to be the most useful catalysts for the reaction of an organic hydroperoxide with an olefin.

Sheldon found that rhenium heptoxide, in contrast to other transition metal compounds, caused rapid, nonproductive decomposition of the hydroperoxide. Thus, an attempt to epoxidize 1-octene with t-butyl hydroperoxide using rhenium heptoxide gave complete conversion of the hydroperoxide to the corresponding alcohol but none of the desired epoxide product. Kollar [U.S. Pat. No. 3,351,635 (Table I); *Preprints, Dev. Pet. Chem.* 106(1978)] also reported extremely low yields of epoxide when the use of a rhenium catalyst in an epoxidation reaction was attempted, apparently due to the very rapid decomposition of the hydroperoxide catalyzed by the rhenium compound. Low selectivity to epoxide was similarly observed using rhenium decacarbonyl as catalyst, cyclohexene as the olefin substrate, and t-butyl hydroperoxide as the oxidant [Rummel et al. *Oxid. Commun.* 6, 319(1984)]. Jorgensen, in a recent review of transition metal catalyzed epoxidations [*Chem. Rev.* 89, 431(1989)], concludes that rhenium complexes are poor epoxidation catalysts using t-butyl hydroperoxide as oxidant.

To date, rhenium compounds such as rhenium heptoxide have thus been primarily used to promote decomposition reactions of hydroperoxides rather than as oxidation catalysts. For example, European Pat. Appl No. 308,101 employed rhenium compounds to catalyze the decomposition of t-butyl hydroperoxide to t-butyl alcohol. Jpn. Kokai No. 63-277,640 (*Chem Abst* 110:172753d) teaches cyclohexyl hydroperoxide decomposition to cyclohexanol or cyclohexanone using rhenium heptoxide. U.S. Pat. No. 4,297,518 describes the use of rhenium heptoxide to catalyze the rearrangement of cumene hydroperoxide to phenol and acetone.

It is thus apparent that rhenium compounds have heretofore been found to be of little utility as catalysts for the epoxidation of olefins using alkyl hydroperoxides as the source of oxygen, owing to the tendency of such compounds to favor hydroperoxide decomposition over olefin epoxidation. We have now found that certain rhenium porphyrin complexes, in contrast to the rhenium compounds employed in the prior art, are excellent olefin epoxidation catalysts and permit the preparation of epoxides with high selectivity and minimal unproductive hydroperoxide decomposition.

DETAILED DESCRIPTION OF THE INVENTION

The catalyst employed in the process of this invention is an oxorhenium (V) porphyrin complex. Such compounds are well-known and contain at least one rhenium center in a +5 oxidation state. The rhenium has at least one oxygen atom bonded to it and is coordinated by a porphyrin ligand. Preferably, the oxorhenium (V) porphyrin complex catalyst has the general structure ORe(P)X, a mononuclear complex, or [ORe(P)]₂O, an oxygen bridged binuclear complex P is a porphyrin ligand, that is, a cyclic structure comprised of four pyrrole rings X is an anion (i.e., an ion having a negative charge), preferably selected from the group consisting of halide (e.g., fluoride, chloride, bromide, iodide $C_6H_5CH_2O-$), alkoxide (e.g., methoxide, ethoxide, isopropoxide, t-butoxide), phenoxide (e.g., $C_6H_5O-$ or a substituted ArO—), hydroxide, carboxylate (e.g., acetate, propionate, acetyl acetonate, oxalate), thiocyanate, perchlorate, cyanate, nitrate, nitrite, phosphate, and sulfate. The porphyrin ligand is desirably selected from the group consisting of 5,10,15,20-tetraphenyl porphyrin, 5,10,15,20-tetra(p-tolyl)porphyrin, 5,10,15,20-tetra(p-anisyl)porphyrin, 5,10,15,20-tetra(p-chlorophenyl)porphyrin, 2,3,7,8,12,13,17,18-octaethyl porphyrin, 5,10,15,20-tetramesityl porphyrin, and 5,10,15,20-tetra(2,6-dichlorophenyl)porphyrin. However, other porphyrin ligands having a variety of different substituents on the porphyrin ring will also be suitable for use and the activity of the rhenium porphyrin catalyst may be altered as desired by varying the identity and position of the porphyrin substituents. Useful substituents include, for example, phenyl, pyridyl, halide, hydroxy, carboxy, cyano, amino, alkoxy, phenoxy, nitro, alkyl, sulfonyl, or combinations thereof such as halophenyl or amino alkyl.

Illustrative oxorhenium porphyrin complexes useful as catalysts in the practice of the invention include:

| | |
|---|---|
| [ORe(TTP)]$_2$O | [ORe(TPP)]$_2$O |
| ORe(TTP)OMe | ORe(TAP)OCH$_3$ |
| ORe(TTP)Cl | ORe(TpClP)OCH$_3$ |
| ORe(TTP)F | ORe(OEP)OAc |
| ORe(TTP)Br | ORe(TMP)Cl |
| ORe(TTP)I | ORe(OEP)OPh |
| ORe(TTP)OCN | [ORe(OEP)]$_2$O |
| ORe(TTP)NCS | ORe(OEP)OBz |
| ORe(TTP)OClO$_3$ | ORe(OEP)F |
| ORe(TTP)OEt | ORe(OEP)Cl |
| ORe(TTP)OiPr | [ORe(TAP)]$_2$O |
| ORe(TTP)OtBu | ORe(TMP)OAc |
| ORe(TTP)OAc | ORe(TMP)OH |
| ORe(TTP)OMe | [ORe(TpClP)]$_2$O |
| ORe(TPP)OAc | ORe(TPP)Cl |
| ORe(TPP)OClO$_3$ | ORe(TPP)Br | wherein
TTP=5,10,15,20-tetra(p-toly)prophyrin
TPP=5,10,15,20-tetraphenyl prophyrin
TAP=5,10,15,20-tetra(p-anisyl)porphyrin
TpClP=5,10,15,20-tetra(p-chlorophenyl)porphyrin
OEP=2,3,7,,12,13,17,18-octaethyl porphyrin
TMP=5,10,15,20-tetramesityl porphyrin
OMe=methoxide
Cl=chloride
F=fluoride
Br=bromide
I=iodide
OCN=cyanate
NCS=thiocyanate
OClO$_3$=perchlorate
OEt=ethoxide
OiPr=isopropoxide
OtBu=t-butoxide
OAc=acetate
OPh=phenoxide
OBz=$C_6H_5CH_2O-$ Procedures for the synthetic preparation of oxorhenium porphyrin complexes useful as catalysts in the process of this invention are found in the following publications, all of which are incorporated herein by reference in their entirety: Buchler et al. *Chem. Ber.* 106, 2710(1973); Buchler et al. *Z. Naturforsch* B. 45, 518(1990); Buchler et al. *Inorg. Nucl. Lett.* 8, 1073(1972); Murakami et al. *Kenkyu Hokoku- Ashai Garasu Kogyo Gijutsu Shorei Kai* 34, 295(1979); European Pat. Appl. No. 308,791; and U.S. Pat. No. 4,987,226.

The amount of oxorhenium porphyrin complex used in the process of this invention is not critical, but should be sufficient to catalyze the oxidation of the olefin substrate by the organic hydroperoxide. Molar ratios of olefin:catalyst of from about 10,000:1 to 1:1 will generally be appropriate for achieving useful yields of epoxide within commercially feasible reaction times, owing to the relatively high catalytic activity of the rhenium porphyrin complexes. Preferably, however, the olefin:catalyst molar ratio is from about 2000:1 to about 50:1.

The organic hydroperoxide to be used as the oxidizing agent in the process of this invention may be any organic compound having at least one hydroperoxy functional group (—OOH). Secondary and tertiary hydroperoxides are preferred, however, owing to the higher instability and greater safety hazards associated with primary hydroperoxides. The organic hydroperoxide preferably has the general structure

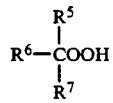

wherein $R^5$, $R^6$, and $R^7$ are the same or different and are selected from the group consisting of hydrogen, methyl, ethyl, and phenyl. Exemplary organic hydroperoxides include t-butyl hydroperoxide, t-amyl hydroperoxide, cumene hydroperoxide, ethyl benzene hydroperoxide, cyclohexane hydroperoxide, methyl cyclohexane hydroperoxide, tetralin hydroperoxide, isobutyl benzene hydroperoxide, ethyl naphthalene hydroperoxide, and the like. Mixtures of organic hydroperoxides may also be employed. The amount of organic hydroperoxide is not critical, but most suitably the molar ratio of olefin:organic hydroperoxide is suitably from about 100:1 to 1:100 when the olefin contains one ethylenically unsaturated group. The molar ratio of ethylenically unsaturated groups in the olefin substrate to organic hydroperoxide is more preferably in the range of from 20:1 to 1:5. One equivalent of hydroperoxide is theoretically required to oxidize one equivalent of a mono-unsaturated olefin substrate, but it may be desirable to employ an excess of olefin to optimize selectivity to the epoxide.

The olefin substrate may be any organic compound having at least one ethylenically unsaturated functional group (i.e., a carbon-carbon double bond) and may be an aromatic, aliphatic, mixed aromatic-aliphatic (e.g., aralkyl), cyclic, branched or straight chain olefin. Preferably, the olefin contains from 2 to 30 carbon atoms (i.e., a $C_2$-$C_{30}$ olefin). More than one carbon-carbon double bond may be present in the olefin; dienes, trienes, and other polyunsaturated substrates thus may be used. Other examples of suitable substrates include unsaturated fatty acids or fatty acid derivatives such as esters or glycerides and oligomeric or polymeric unsaturated compounds such as polybutadiene.

The olefin may contain substituents other than hydrocarbon substituents such as halide, carboxylic acid, ether, hydroxy, thiol, nitro, cyano, ketone, ester, anhydride, amino, and the like.

Exemplary olefins suitable for use in the process of this invention include ethylene, propylene, the butenes, butadiene, the pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene, 1-octadecene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, oleostearic acid, myristic acid, palmitic acid, and ricinoleic acid and their esters.

The process of this invention is particularly well suited for the epoxidation of olefins wherein the ethylenically unsaturated functional group of the olefin bears at least one aromatic substituent. The aromatic substituent may be phenyl, substituted phenyl such as halo phenyl, alkyl phenyl, or alkoxy phenyl, naphthyl, or substituted naphthyl, or the like. Particularly preferred are alkenyl aromatic compounds, especially those having the general structure

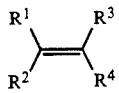

wherein at least one of $R^1$, $R^2$, $R^3$, or $R^4$ is an aromatic substituent and the remaining R substituents are selected from the group consisting of hydrogen and $C_1-C_8$ alkyl. Examples of alkenyl aromatic compounds include styrene, α-methyl styrene, β-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methylstyrene, ar-ethyl styrene, ar-tert-butyl styrene, ar-chlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like.

An organic solvent or mixture of organic solvents may additionally be present when the olefin is contacted with the hydroperoxide and catalyst. The solvent may be used to dilute, disperse, or dissolve the components of the reaction mixture, thus providing better temperature control or faster reaction rates. The identity of the solvent may advantageously be altered to control the rate or selectivity of the epoxidation process. Examples of suitable organic solvents include, but are not limited to, aliphatic hydrocarbons (e.g., hexane, cyclohexane, petroleum ether), aromatic hydrocarbons (e.g., benzene, toluene, xylene, ethyl benzene, cumene), and halogenated hydrocarbons (e.g., methylene chloride, chloroform, chlorobenzene). If direct production of the glycol corresponding to an epoxide is desired, water may be deliberately introduced into the epoxidation reaction mixture for this purpose. It is generally desirable to carry out the process of this invention under an inert atmosphere, that is, in the absence of oxygen.

An unexpected advantage of the process of this invention is the reduced tendency of the rhenium porphyrin catalyst as compared to other epoxidation catalysts to be inhibited by water, alcohol, ethers, or other Lewis bases in the reaction mixture. It is well known that other transition metal epoxidation catalysts such as molybdenum coordinate strongly with Lewis bases, thereby reducing the rate of reaction. Since the organic hydroperoxide is converted to an alcohol as the epoxidation reaction proceeds, pushing the epoxidation to high conversion can consequently be difficult. This is a particular problem if a relatively high boiling epoxide is the desired product, since such epoxides are difficult to separate from a reaction mixture containing large amounts of unreacted olefin and hydroperoxide. In contrast, the use of the rhenium porphyrin catalysts of this invention permits high yields of epoxide to be attained in a batch-type process since such catalysts are inhibited to a much lesser extent than prior art epoxidation catalysts.

The reaction temperature is not critical, but should be sufficient to accomplish substantial conversion of the olefin to epoxide within a reasonably short period of time. It is generally advantageous to carry out the reaction to achieve as high a hydroperoxide conversion as possible, preferably at least 50% and desirably at least 90%, consistent with reasonable selectivities. The optimum reaction temperature will be influenced by catalyst activity, olefin reactivity, reactant concentrations, and type of solvent employed, among other factors, but typically will be in a range of from about 0° C. to 150° C. More preferably, the temperature will be from about 20° C. to 100° C. Reaction times of from about 10 minutes to 48 hours will typically be appropriate, depending upon the above-identified variables. Although subatmospheric pressures can be employed, the reaction is preferably performed at atmospheric pressure or at elevated pressure (typically, not greater than about 2,000 psig). Generally, it will be desirable to maintain the reaction components as a liquid phase mixture.

The process of this invention may be carried out in a batch, continuous, or semi-continuous manner using any appropriate type of reaction vessel or apparatus. Known methods for conducting transition metal catalyzed epoxidations of olefins using organic hydroperoxides will generally also be suitable for use in this process. Thus, the reactants may be combined all at once or sequentially. For example, the organic hydroperoxide may be added incrementally to the reaction zone. Once the epoxidation has been carried out to the desired degree of conversion, the desired epoxide product may be separated and recovered from the reaction mixture using any appropriate technique such as fractional distillation, extractive distillation, liquid-liquid extraction, crystallization, or the like. The co-product of the reaction will generally be the corresponding alcohol derived from the organic hydroperoxide and may similarly be separated and recovered for use as a valuable product in its own right. For example, t-butyl alcohol will be produced if t-butyl hydroperoxide is employed as the oxidant while methyl benzyl alcohol is obtained using ethyl benzene hydroperoxide. The alcohol product can in turn be readily dehydrated to a useful olefin such as isobutylene or styrene. After separating from the epoxidation reaction mixture, the recovered rhenium porphyrin catalyst may be economically re-used in subsequent epoxidations.

From the foregoing description, one skilled in the art can readily ascertain the essential characteristics of this invention, and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

A mixture containing 0.01 g ORe(P)OMe catalyst [prepared as described in Buchler et al. Z. Naturforsch B 45, 518(1990); P= 5,10,15,20-tetraphenyl porphyrine, 10 g methylene chloride as solvent, 0.25 g trans-methyl styrene, and 1 g of 3 M anhydrous t-butyl hydroperoxide in isooctane was refluxed at 40° C. The reaction was monitored by gas liquid chromatography. After. 2 hours, 28% olefin conversion was observed with 95% selectivity to the corresponding epoxide based on olefin conversion. After 16 hours, 95% olefin conversion was attained. The epoxide selectivity remained remarkably high (94%). This example demonstrates the usefulness of the process of this invention in the preparation of high yields of epoxide from an olefin substrate.

reference cited in Example 1. TBHP is t-butyl hydroperoxide, TBA is t-butyl alcohol, and EBHP is ethyl benzene hydroperoxide. The results obtained are shown in Table I.

Surprisingly, higher olefin conversions and epoxide selectivities were generally obtained using the process of this invention than when an oxidant such as hydrogen peroxide, N-methyl morpholine N-oxide, or iodosobenzene was used in place of the organic hydroperoxide. This is demonstrated by comparative examples 5,6,10,18 and 19. This result was completely unexpected in view of the prior art recognition that rhenium compounds are generally poor catalysts for olefin epoxidation using an hydroperoxide as the oxidizing agent.

EXAMPLES 22-24

These examples demonstrate the unexpected advantages of using the oxorhenium porphyrin catalysts of this invention in an olefin epoxidation reaction as compared to prior art epoxidation atalysts containing transition metals other than rhenium. Example 1 was repeated using either molybdenum dioxo dipropylene glycolate (Example 22; U.S. Pat. No. 4,772,731), vanadyl acetylacetonate (Example 23), or titanium isopropoxide (Example 24) as catalyst. In each case, the amount of catalyst was adjusted so that the molar ratio of catalyst:olefin was approximately the same. The reaction conditions and amounts of reactants were otherwise the same as described in Example 1. The olefin conversion and selectivity to epoxide were determined after 16 hours, as shown in Table II.

TABLE II

| Ex. No. | Catalyst | Wt, g | Time, hr. | % Olefin Conversion | % Epoxide Selectivity | % Epoxide Yield |
|---|---|---|---|---|---|---|
| 1 | ORe(P)OMe | 0.01 | 16 | 95 | 95 | 90 |
| 22* |  MoO$_2$ | 0.006 | 16 | 80 | 95 | 76 |
| 23* | VO(acac)$_2$ | 0.007 | 19 | 70 | 87 | 61 |
| 24* | Ti(Oi—Pr)$_4$ | 0.01 | 19 | 23 | 94 | 22 |

*comparative example

EXAMPLES 2-21

To illustrate the use of other olefins, hydroperoxides, and rhenium porphyrin catalysts in the process of this invention, additional batch epoxidation runs were performed using the same general procedure described in Example 1. The epoxidations employed 0.5 mole % catalyst based on olefin, methylene chloride solvent, and a reaction temperature of 40° C. (except where noted). Catalyst 1 was ORe(P)Cl, catalyst 2 was ORe(P)OMe, and catalyst 3 was [ORe(P)])]$_2$O wherein P in each case was 5,10,15,20-tetraphenyl porphyrin. The catalysts were prepared as described in the Buchler While all of the catalysts evaluated gave high epoxide selectivity, olefin conversion was significantly higher when the rhenium catalyst was employed as compared to the conversions attained after a similar reaction time using a molybdenum, vanadium, or titanium containing catalyst. As discussed above, this is believed to be due to the reduced tendency of the rhenium catalyst to be inhibited by the alcohol generated during the epoxidation. Thus, the use of the oxorhenium porphyrin complex catalysts of this invention resulted in a greatly improved yield of the epoxide product.

TABLE I

OLEFIN EPOXIDATION WITH OXORHENIUM PORPHYRIN CATALYSTS

| Ex. No. | Olefin | Catalyst | Additive | Oxidant | Time, hr. | % Olefin Conv. | % Epoxide Sel. |
|---|---|---|---|---|---|---|---|
| 2 | 1-Octene | 1 | — | TBHP | 18 | 5 | 20 |
| 3 | 1-Octene | 2 | — | TBHP | 18 | 5 | 20 |
| 4 | 1-Octene | 1 | Imidazole | TBHP | 18 | 5 | 20 |
| 5* | 1-Octene | 1 | — | H$_2$O$_2$/TBA | 18 | <5 | <20 |
| 6* | 1-Octene | 1 | — | Iodosylbenzene | 18 | <5 | <20 |
| 7 | trans-2-Octene | 2 | Imidazole | TBHP | 20 | 10 | 50 |
| 8 | trans-2-Octene | 3 | Imidazole | TBHP | 20 | 10 | 60 |
| 9 | Cyclohexene | 1 | Imidazole | TBHP | 15 | 5 | <20 |
| 10* | Cyclohexene | 3 | — | Iodosylbenzene | 16 | 10 | 0 |
| 11 | 2,3-Dimethyl-2-Butene | 3 | — | TBHP | 18 | 16 | 30 |
| 12 | Styrene | 2 | — | TBHP | 22 | 15 | 60 |

TABLE I-continued

OLEFIN EPOXIDATION WITH OXORHENIUM PORPHYRIN CATALYSTS

| Ex. No. | Olefin | Catalyst | Additive | Oxidant | Time, hr. | % Olefin Conv. | % Epoxide Sel. |
|---|---|---|---|---|---|---|---|
| 13 | α-Methylstyrene | 1 | — | TBHP | 19 | 64 | 65 |
| 14 | α-Methylstyrene | 2 | — | TBHP | 15 | 60 | 65 |
| 15 | trans-β-Methylstyrene | 1 | — | TBHP | 16 | 93 | 94 |
| 16 | trans-β-Methylstyrene | 1 | — | TBHP[b] | 8 | 60 | 85 |
| 17 | trans-β-Methylstyrene | 1 | — | EBHP | 8 | 45 | 86 |
| 18* | trans-β-Methylstyrene | 1 | — | $H_2O_2$/TBA | 8 | <5 | 0 |
| 19* | trans-β-Methylstyrene | 1 | — | Iodosylbenzene | 16 | <5 | 0 |
| 20 | cis-β-Methylstyrene | 1 | — | TBHP | 2 | 15 | 68[a] |
| 21* | cis-β-Methylstyrene | 2 | — | N-Methyl morpholine N-oxide | 18 | <5 | 0 |

Notes:
[a] Epoxidation is not stereoselective, epoxide made is mostly trans.
[b] TBHP/TBA mixture produced in commercial isobutane oxidation process
*Comparative example

We claim:

1. A process for epoxidizing an olefin comprising contacting the olefin with an organic hydroperoxide in the presence of an amount of an oxorhenium (V) porphyrin complex catalyst effective to form an epoxide of the olefin.

2. The process of claim 1 wherein the oxorhenium (V) porphyrin complex catalyst has the general structure ORe(P)X or

[ORe(P)]$_2$O wherein P is a porphyrin ligand and X is an anion selected from the group consisting of halide, alkoxide, phenoxide, hydroxide, carboxylate, thiocyanate, perchlorate, cyanate, nitrate, nitrite, phosphate and sulfate.

3. The process of claim 2 wherein the porphyrin ligand is selected from the group consisting of 5,10,15,20-tetraphenyl porphyrin, 5,10,15,20-tetra(p-tolyl)porphyrin, 5,10,15,20-tetra(p-anisyl)porphyrin, 5,10,15,20-tetra(pchlorophenyl)porphyrin, 5,10,15,20-tetra(p-anisyl)porphyrin, 5,10,15,20-tetramesityl porphyrin, and 5,10,15,20-tetra(2,6-dichlorophenyl)porphyrin.

4. The process of claim 1 wherein the olefin is an alkenyl aromatic compound.

5. The process of claim 1 wherein the olefin has the general structure

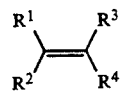

wherein at least one of $R^1$, $R^2$, $R^3$ or $R^4$ is an aromatic substituent and the remaining R substituents are selected from the group consisting of hydrogen and $C_2$-$C_8$ alkyl.

6. The process of claim 1 wherein the organic hydroperoxide is a secondary or tertiary hydroperoxide having the general structure

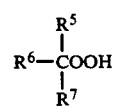

wherein wherein $R^5$, $R^6$, and $R^7$ are the same or different and are selected from the group consisting of hydrogen, methyl, ethyl, and phenyl.

7. A process for epoxidizing an olefin wherein at least one of the ethylenically unsaturated functional groups of the olefin bears an aromatic substituent, said process comprising contacting the olefin with a secondary or tertiary organic hydroperoxide having the general structure

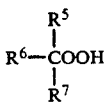

wherein $R^5$, $R^6$, and $R^7$ are the same or different and are selected from the group consisting of hydrogen, methyl, ethyl, and phenyl in the presence of an amount of an oxorhenium (V) porphyrin complex catalyst having the general structure ORe(P)X or

[ORe(P)]$_2$O wherein P is a porphyrin ligand and X is an anion selected from the group consisting of halide, alkoxide, phenoxide, hydroxide, perchlorate, thiocyanate, cyanate, and carboxylate effective to form an epoxide of the olefin.

8. The process of claim 7 wherein the olefin has the general structure

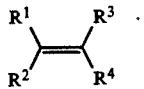

wherein at least one of $R^1$, $R^2$, $R^3$, or $R^4$ is an aromatic substituent and the remaining R substituents are selected from the group consisting of hydrogen and $C_1$-$C_8$ alkyl.

9. The process of claim 8 wherein the aromatic substituent is phenyl.

10. The process of claim 7 wherein the secondary or tertiary organic hydroperoxide is selected from the group consisting of t-butyl hydroperoxide, t-amyl hydroperoxide, cumene hydroperoxide, and ethyl benzene hydroperoxide.

11. The process of claim 7 wherein the molar ratio of olefin:organic hydroperoxide is from about 100:1 to 1:100.

12. The process of claim 7 wherein the porphyrin ligand is selected from the group consisting of 5,10,15,20-tetraphenyl porphyrin 9,10,15,20-tetra(p-tolyl)porphyrin, 5,10,15,20-tetra(p-anisyl)porphyrin, 5,10,15,20-tetra(p-chlorophenyl)porphyrin, 2,3,7,8,12,13,17,18-octaethyl porphyrin, 5,10,15,20-tetramesityl porphyrin, and 5,10,15,20-tetra(2,6-dichlorophenyl)porphyrin.

13. The process of claim 7 wherein the molar ratio of olefin:oxorhenium (V) porphyrin complex catalyst is from about 10,000:1 to 1:1.

14. The process of claim 7 wherein said contacting is carried out at a temperature of from about 0° C to 150° C.

15. The process of claim 7 wherein said contacting is carried out for a time of from about 10 minutes to about 48 hours.

16. The process of claim 7 wherein an organic solvent is additionally present during said contacting.

17. A process for epoxidizing an olefin having the general structure

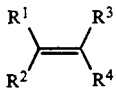

wherein at least one of $R^1$, $R^2$, $R^3$, or $R^4$ is an aromatic substituent and the remaining R substituents are selected from the group consisting of hydrogen and $C_1$–$C_8$ alkyl, said process comprising contacting the olefin with an organic hydroperoxide selected from the group consisting of t-butyl hydroperoxide, cyclohexane hydroperoxide, cumene hydroperoxide, and ethyl benzene hydroperoxide in the presence of an oxorhenium (V) porphyrin complex catalyst having the general structure ORe(P)

or

[ORe(P)]$_2$O wherein P is a porphyrin ligand selected from the group consisting of 5,10,15,20-tetraphenyl porphyrin, 5,10,15,20-tetra(p-tolyl)porphyrin, 5,10,15,20-tetra(p-anisyl)porphyrin, 5,10,15,20-tetra(p-chlorophenyl)porphyrin, 2,3,7,8,12,13,17,18-octaethyl porphyrin, 5,10,15,20-tetramesityl porphyrin, and 5,10,15,20-tetra(2,6-dichlorophenyl)porphyrin, and X is an anion selected from the group consisting of halide, alkoxide, phenoxide, hydroxide, and carboxylate and an organic solvent at a temperature of from about 0° C. to 150° C. and from a time of from about 10 minutes to about 48 hours to form an epoxide of the olefin, wherein the molar ratio of olefin:organic hydroperoxide is from about 100:1 to 1:100 and the molar ratio of olefin:oxorhenium (V) porphyrin complex catalyst is from about 10,000:1 to 1:1.

18. The process of claim 17 wherein said temperature is from about 20° C. to 100° C.

19. The process of claim 17 wherein the molar ratio of olefin:oxorhenium (V) porphyrin complex catalyst is from about 2000:1 to about 50:1.

20. The process of claim 17 wherein R is phenyl and $R^2$, $R^3$, and $R^4$ are the same or different and are methyl or hydrogen.

* * * * *

UNITED STATES PATENT AND TRADEMARK OFFICE
CERTIFICATE OF CORRECTION

PATENT NO. : 5,103,027

DATED : April 7, 1992

INVENTOR(S) : Wilfred P. Shum, et al

It is certified that error appears in the above-identified patent and that said Letters Patent is hereby corrected as shown below:

Title page, item [54], and column 1, line 2, delete "EXPOXIDATION" and insert --EPOXIDATION--.

Signed and Sealed this

Twenty-second Day of June, 1993

Attest:

MICHAEL K. KIRK

*Attesting Officer*   Acting Commissioner of Patents and Trademarks